(12) United States Patent
de Paz Sicam et al.

(10) Patent No.: US 9,004,689 B2
(45) Date of Patent: Apr. 14, 2015

(54) APPARATUS FOR CORNEAL SHAPE ANALYSIS AND METHOD FOR DETERMINING A CORNEAL THICKNESS

(75) Inventors: Victor Arni de Paz Sicam, Rotterdam (NL); Gerrit Ludolph van der Heijde, Muiderberg (NL); Michiel Herman Mensink, S-Gravenhage (NL)

(73) Assignee: Vereniging Vu-Windesheim, Amsterdam (NL)

( * ) Notice: Subject to any disclaimer, the term of this patent is extended or adjusted under 35 U.S.C. 154(b) by 847 days.

(21) Appl. No.: 12/937,816

(22) PCT Filed: Apr. 16, 2009

(86) PCT No.: PCT/EP2009/002977
§ 371 (c)(1),
(2), (4) Date: Dec. 27, 2010

(87) PCT Pub. No.: WO2009/127442
PCT Pub. Date: Oct. 22, 2009

(65) Prior Publication Data
US 2011/0105943 A1    May 5, 2011

(30) Foreign Application Priority Data
Apr. 17, 2008  (EP) .................................... 08075303

(51) Int. Cl.
*A61B 3/10* (2006.01)
*A61B 3/14* (2006.01)
*A61B 13/00* (2006.01)
*A61B 3/00* (2006.01)

(52) U.S. Cl.
CPC ............. *A61B 3/1005* (2013.01); *A61B 3/0025* (2013.01)

(58) Field of Classification Search
USPC ............ 600/452, 558, 398–406; 250/559.27, 250/559.29; 351/205–212; 356/125, 126; 606/5
See application file for complete search history.

(56) References Cited

U.S. PATENT DOCUMENTS 5,054,907 A * 10/1991 Sklar et al. .................... 351/212
5,475,452 A * 12/1995 Kuhn et al. .................... 351/212
(Continued)

FOREIGN PATENT DOCUMENTS

EP    1632169 A2    3/2006
GB    1209451 A     10/1970

OTHER PUBLICATIONS

Jason Turuwhenua, Corneal surface reconstruction algorithm using Zernike polynomial representation: improvements, vol. 24, No. 6/Jun. 2007/J Opt. Soc. Am.A., 1551-1561.
(Continued)

*Primary Examiner* — Devin Henson
(74) *Attorney, Agent, or Firm* — Hoffmann & Baron, LLP

(57) ABSTRACT

A method of determining a corneal thickness and an apparatus for determining said is provided. The method comprises the following the steps: —illuminating a cornea by a plurality of stimulator point light sources, capturing an image of the cornea comprising reflected images of the stimulator point light sources, obtaining a model representing an anterior surface of the cornea, —constructing a second model representing a posterior surface of the cornea from the image by raytracing the reflected images of the stimulator point light sources towards the model representing the anterior surface of the cornea, determining the corneal thickness from the model representing the anterior surface and the second model representing the posterior surface.

28 Claims, 5 Drawing Sheets

(56) References Cited

U.S. PATENT DOCUMENTS

| | | | |
|---|---|---|---|
| 5,865,832 A * | 2/1999 | Knopp et al. | 606/10 |
| 5,867,250 A | 2/1999 | Baron | |
| 6,193,371 B1 | 2/2001 | Snook | |
| 6,692,126 B1 * | 2/2004 | Xie et al. | 351/212 |
| 7,252,380 B2 * | 8/2007 | Koest | 351/205 |
| 7,497,575 B2 * | 3/2009 | Huang et al. | 351/206 |
| 7,896,497 B2 * | 3/2011 | McBeth | 351/212 |
| 2004/0021826 A1 | 2/2004 | Sarver et al. | |
| 2005/0281440 A1 | 12/2005 | Pemer | |
| 2011/0273669 A1 * | 11/2011 | Abitbol et al. | 351/212 |

OTHER PUBLICATIONS

Helen Owens, PhD., et al., Posterior Corneal Changes with Orthokeratology, Optometry and Vision Science vol. 81 No. 6 Jun. 2004, 421-426.

Jason Turuwhenua, PhD, et al., The Recovery of Posterior Cornea and Anterior Lens Radii by a Novel Ray-Tracing Method, Optometry and Vision Science, vol. 81 No. 11 Nov. 2004.

* cited by examiner

APPARATUS FOR CORNEAL SHAPE ANALYSIS AND METHOD FOR DETERMINING A CORNEAL THICKNESS

CROSS-REFERENCE TO RELATED APPLICATIONS

This application is the National Stage of International Application No. PCT/EP2009/002977, filed Apr. 16, 2009, which claims the benefit of European Application No. EP 08075303.1, filed Apr. 17, 2008, the contents of which is incorporated by reference herein.

BACKGROUND OF THE INVENTION

Determination of a corneal thickness is important for various diagnostic applications as well as an important part of various surgical interventions on the eye. A method and apparatus for obtaining such a thickness is e.g. known from U.S. Pat. No. 6,692,126. The apparatus disclosed applies a Placido ring illuminator to illuminate the cornea and derives a model of the anterior surface of the cornea from the image obtained. By projecting thin slits of light on the cornea, a second image can be taken and used to determine the corneal thickness from the model of the anterior surface and the second image.

The apparatus and method as known in the art suffers from a number of drawbacks. First of all, this system needs to focus on two different planes: firstly the iris plane for imaging the reflections of the Placido illuminator, and secondly the cornea plane for imaging the cornea, which is partially illuminated by the slits of light. This system therefore requires the use of two camera's or one camera with a rapidly moving lens. This will drive up complexity and costs of the camera.

Second, it is known that the use of a Placido ring illuminator requires some assumptions with respect to the corneal anterior surface. Due to the use of ring shaped light sources, a one-to-one correspondence between a point on the stimulator source (i.e. the Placido ring illuminator) and a point on the captured image cannot be determined unless certain symmetries in the corneal surface are assumed. As in reality, these assumed symmetries may not be present; inaccuracies may be introduced in the model. As the model is further on applied to determine the corneal thickness, inaccuracies in this thickness due to the assumed symmetries of the anterior surface may occur as well. It can further be noted that the use of slit-shaped illumination sources results in a similar problem in that a one to one correspondence between a point on the stimulator source (i.e. the slit-shaped illumination source) and a point on the captured image may be difficult to establish. A further drawback of the apparatus as known in the art is the requirement of sequentially capturing two images of the cornea to determine the corneal thickness. In case of a displacement of the eye between the capturing of the first and the second image, some uncertainty with respect to the position of the anterior surface of the cornea may exist when the second image is taken. This uncertainty may further introduce inaccuracies in the determination of the corneal thickness. As an alternative, it is proposed in U.S. Pat. No. 6,692,126 to use a camera system with multiple camera's each camera being arranged to record an image of one of the illumination sources. This may result in a more complex and therefore more expensive apparatus.

It is further acknowledged that other apparatuses exist for approximating a corneal thickness. One of such apparatuses is described in Optometry and Vision science, Vol. 67, No. 10, pp. 757-763 and uses a plurality of stimulator points for illuminating the cornea. The image obtained is used to estimate the corneal thickness by assuming that both the anterior surface and the posterior surface are spherical surfaces.

It is an object of the present invention to provide an apparatus for corneal diagnosis and a method for determining a corneal thickness that alleviates, at least partly, one or more of the drawbacks mentioned above.

SUMMARY OF THE INVENTION

According to an aspect of the invention, there is provided a method of determining a corneal thickness comprising the steps of
  illuminating a cornea by a plurality of stimulator point light sources,
  capturing an image of the cornea comprising reflected images of the stimulator point light sources,
  obtaining a model representing an anterior surface of the cornea,
  constructing a second model representing a posterior surface of the cornea from the image by ray-tracing the reflected images of the stimulator point light sources towards the model representing the anterior surface of the cornea,
  determining the corneal thickness from the model representing the anterior surface and the second model representing the posterior surface.

Compared to the methods as known in the art, in the method according to the invention the construction of the posterior surface model is obtained by applying ray-tracing techniques to an image obtained by illuminating the cornea using a plurality of stimulator point light sources, rather than using slit-shaped illumination sources. Using ray-tracing techniques on an image obtained from stimulator point light sources facilitates the construction of the posterior surface model as it enables a one-to-one correspondence between a point on the stimulator source (i.e. the stimulator point light sources) and the reflected images of said light sources on the captured image. As such, no approximations or assumptions need to be made regarding the shape of the corneal surface. As a result, the method according to the invention enables a more accurate determination of the posterior surface compared to conventional methods. It can be noted that the method according to the present invention may e.g. apply an anterior surface model obtained from e.g. a conventional corneal topographer (e.g. a topographer designed for determining only shape of anterior cornea surface).

In a preferred embodiment of the method according to the invention, the model representing the anterior surface of the cornea is obtained by:
  capturing a corneal image obtained by illuminating the cornea with a stimulator source,
  using ray-tracing to determine a point of reflection of the stimulator source on the anterior surface,
  performing a fitting algorithm of the point of reflection to a mathematical model to obtain the model representing the anterior surface of the cornea.

It can be noted that the stimulator source may be of different types:
1) source that produces collimated beam,
2) general point source.

For the second case, ray tracing of the second Purkinje image does not necessarily coincide with the chief ray corresponding to the first Purkinje image. This means that if the anterior surface is well reconstructed using the first Purkinje images, the second Purkinje image is sufficient to reconstruct the posterior surface of the cornea. This provides for a simpler surface reconstruction compared to using slit sources because the complex correction for the combined effect of distortion and refraction is not necessary.

It can be noted that the corneal thickness as obtained can e.g. take the form of a table or array providing the corneal thickness at one or more points on the cornea. Said point or points can e.g. correspond to points on the anterior surface or the posterior surface. As such, the corneal thickness provides information on the distance between the anterior and posterior surface of the cornea at a number of points of the cornea. This information can e.g. be applied by a surgeon to determine which interventions to the eye are possible. Equally, the thickness can be presented as a function fitted to the corneal thickness as determined at a number of points.

According to another aspect of the invention, there is provided an apparatus for corneal shape analysis, the apparatus comprising
- a plurality of stimulator point light sources for, in use, illuminating a cornea of an eye,
- a camera system for capturing reflected images of the stimulator point light sources,
- a computational unit for, in use, performing the following steps
  - obtaining a model of an anterior surface of the cornea,
  - constructing a second model representing the posterior surface of the cornea by ray-tracing the reflected images of the stimulator point light sources towards the model representing the anterior surface of the cornea and
  - determining a corneal thickness from the model representing the anterior surface and the second model representing the posterior surface.

By applying ray-tracing techniques on an image comprising the reflected images of a plurality of stimulator point light sources to determine a model representing the posterior surface of a cornea, a more accurate model can be obtained compared the model obtained by using conventional apparatuses for corneal diagnosis.

It can further be noted that the apparatus according to the invention may equally be applied to determine a model of the anterior surface of the cornea, thereby eliminating either the requirement for a separate apparatus for obtaining said model or the requirement of an additional illumination source (e.g. a Placido ring illuminator) for determining said model.

In a preferred apparatus according to the invention, the camera system is arranged to capture a first image comprising reflected images of the stimulator point light sources and to capture a second image comprising reflected images of the stimulator point light sources, the computational unit further being arranged to, in use,
- obtain the model of an anterior surface of the cornea using the first image and
- construct the second model representing the posterior surface using the second image.

In a yet further embodiment of the apparatus according to the invention, the apparatus further comprises a control unit for setting an illumination level of the stimulator point light sources thereby enabling the first and second image to be captured with a different illumination level.

As will be explained further, it may be advantageous to have a different illumination level for the first and second image, said images being used, in a preferred embodiment of the invention to construct the models of the anterior and posterior surfaces of the cornea.

DETAILED DESCRIPTION OF THE INVENTION

Figure 1:
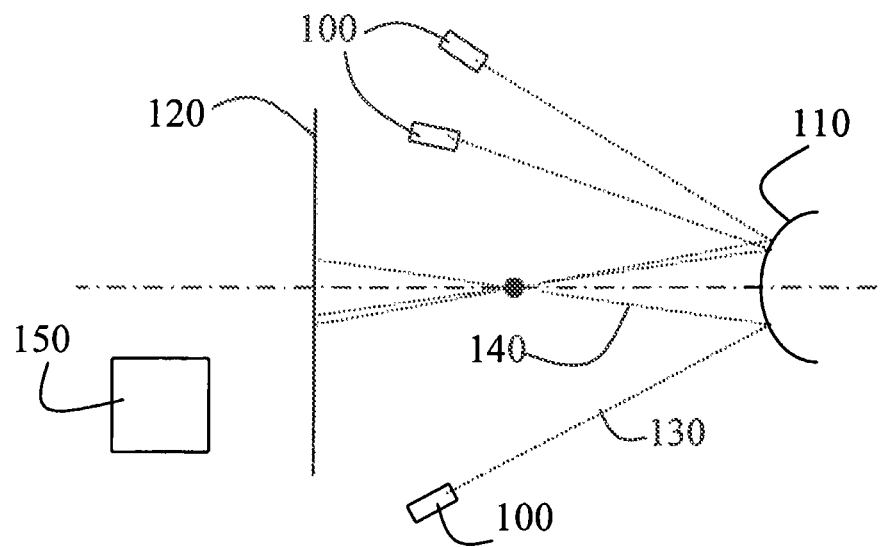
FIG. 1 schematically depicts a first embodiment of an apparatus for corneal diagnosis according to the invention.

FIG. 1 schematically depicts a first embodiment of an apparatus for corneal diagnosis according to the invention. The apparatus comprises a plurality of stimulator point light sources 100 arranged to, in use, illuminate a cornea of an eye. Contour 110 schematically represent the anterior surface of the cornea. The apparatus further comprises a camera system 120 arranged to capture an image of the reflections of the stimulator point light sources on the cornea. FIG. 1 further schematically depicts rays of light 130 originating from the plurality of stimulator point light sources and directed towards the cornea and the corresponding reflected rays 140 on the anterior surface 110 of the cornea. The apparatus as shown in FIG. 1 further comprises a computation unit 150 arranged to process an image obtained from the camera system in such manner that a corneal thickness is obtained. In an embodiment of the present invention, the computational unit 150 is arranged to perform the following steps:

1. obtaining a model of an anterior surface of the cornea,
2. constructing a second model representing the posterior surface of the cornea by ray-tracing the reflected images of the stimulator points towards the model representing the anterior surface of the cornea and
3. determining the corneal thickness from the model representing the anterior surface and the reconstructed posterior surface.

In order to perform step 1, as an example, the computational unit can be arranged to receive a model representing the anterior surface. Said model can e.g. be obtained by analysing the anterior surface of the cornea with a conventional corneal topographer. Such a topographer can e.g. apply a Placido ring illuminator as a stimulator source for illuminating the cornea. Such a model can e.g. take the form of a mathematical model describing the anterior surface. Examples of such mathematical models are spherical models, models using spline functions or Zernike polynomials.

In a preferred embodiment, step 1 is preceded by a step of determining the centre of gravity of all reflected light sources.

Once the model of the anterior surface is obtained, the computational unit of the apparatus according to the invention can use the model representing the anterior surface together with a captured image of the reflections of the stimulator point light sources, to determine a model of the posterior surface of the cornea by using ray-tracing techniques. Examples of ray-tracing methods as applied in the present invention are described further on. The model of the posterior surface may equally take the form of a mathematical model similar to the anterior surface model. Once both the anterior surface and the posterior surface model are established, the corneal thickness can be determined. Starting from either the anterior surface or the posterior surface, the smallest distance towards the other of the two surfaces can be determined for each point of interest, said smallest distance corresponding to the corneal thickness at said point.

In the apparatus according the invention, the cornea is illuminated by stimulator point light sources. Contrary to known light sources such as Placido ring illuminators or slit-lamp illuminators, stimulator point light sources cause a reflection of a single spot only instead of a region (such as a ring or slit). As a consequence, a one to one correspondence between the illumination light source coordinates and the coordinates of the image of said light source as captured by the camera system can easily be established. This is important as it enables a more accurate ray-tracing between the illumination source and the captured image.

Instead of obtaining the model representing the anterior surface from e.g. a corneal analysis using a conventional topographer, the apparatus according to the invention may be applied to determine the anterior surface model, using the stimulator point light sources. In this case, the anterior surface model can e.g. be obtained from the same image as used to determine the posterior surface model thereby eliminating any uncertainty with respect to the position of the eye.

As an alternative, two different images can be taken by the camera system of the apparatus according to the invention, one image for obtaining the model of the corneal surface, and another one for determining the model representing the posterior surface. The images can advantageously be formed using different illumination levels. In a preferred embodiment, the apparatus according to the invention may therefore comprise a control unit for determining the illumination level of the stimulation point light sources. In a preferred embodiment, such a control unit may further be arranged to selectively enable the stimulator point light sources. As such, a first sub set of the stimulator point light sources can e.g. be selected and applied to generate a first image at a predetermined illumination level, said image being used to generate a model representing the anterior surface. Thereafter, a second image can be generated by e.g. illuminating the cornea with either the same or a different sub set of stimulator point light sources (e.g. at a different illumination level), said image being used to determine a second model representing the posterior surface of the cornea. The control unit as applied in a preferred embodiment of the apparatus according to the invention may equally be applied to control the duration of the illumination. As such, the apparatus according to the invention can be arranged to (very) briefly set an illumination level for a part of the stimulator's light sources in order to generate a first image optimized for detecting the shape of the anterior cornea, and secondly for selecting and setting an different but equally brief illumination level for a part of the stimulator's light sources in order to generate a second image optimized for detecting the shape of the posterior cornea. As the eye position may change between the capturing of the two images, the preferred apparatus according to the invention may therefore comprise a camera system for capturing in rapid succession two reflected images of the stimulator point light sources,
    a computational unit for, in use, performing the following additional step
        verifying whether a substantial eye movement has occurred based on comparing and analyzing the position of the iris in both images, Contrary to the prior art, in a preferred embodiment of the present invention, it is possible to use a one camera system with a fixed lens—the camera system being arranged such that a focal plane substantially corresponds to the iris plane for determining the shape of both surfaces.

In a preferred embodiment, the stimulator point light sources may comprise sources projecting beams which are constricted in size and aimed at the pupil in order to substantially avoid illuminating the iris, therewith increasing contrast between $2^{nd}$ Purkinje images and iris.

In a preferred embodiment of the apparatus according to the present invention, the stimulator point light sources comprise one or more LED light sources. The brightness and illumination duration of such LED sources are easily controllable. In addition, LEDs can, due to their size, advantageously be applied to provide a large multitude of stimulator point light sources.

As an alternative, laser diodes or conventional light sources with point-like apertures can be applied to provide light beams to illuminate the cornea.

It can further be noted that a single light source can be used to generate the plurality of stimulator point light sources. As an example, optical fibres and beam splitting techniques can be applied to provide multiple stimulator point light sources originating from a single light source such as a LED, a laser diode or a collimated light source.

Figure 2:
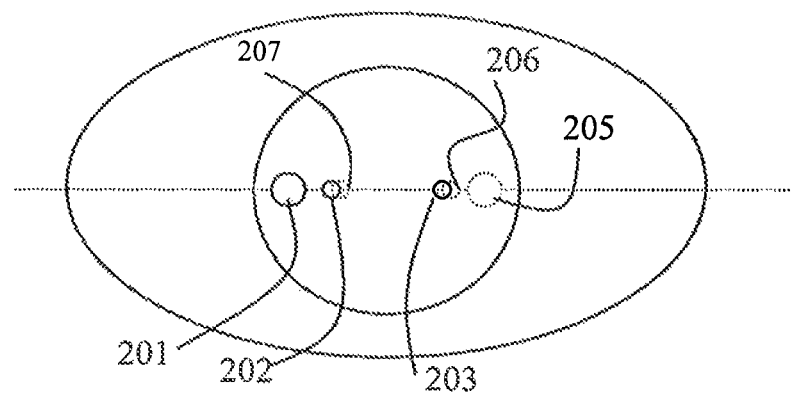
FIG. 2 schematically depicts first, second and fourth Purkinje images originating from two diametrically opposed stimulator point light sources.
Figure 3:
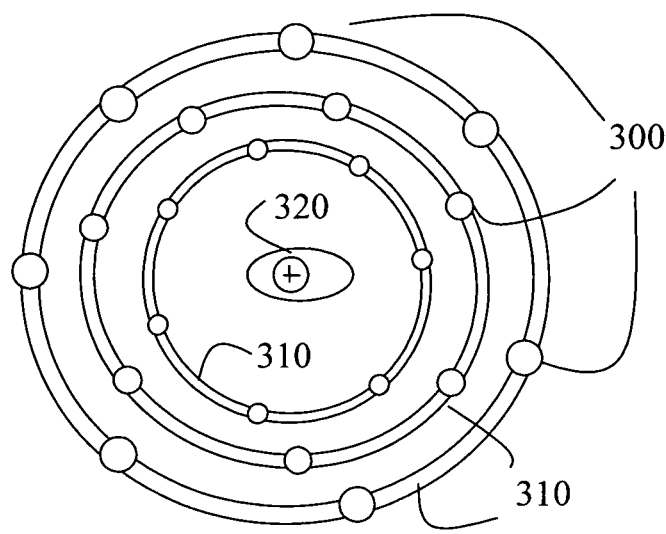
FIG. 3 schematically depicts an arrangement of the stimulator point light sources of an apparatus for corneal diagnosis according to the invention.

In a preferred embodiment of the present invention, the plurality of stimulator point light sources are located on one or more concentric circles, said circles being arranged such that the distance towards the cornea of the stimulator point light sources on a circle is the same for all sources. Such an arrangement facilitates the determination of the model of the posterior surface. In a yet further preferred embodiment, diagonals that can be constructed from the various stimulator point light sources do not coincide. As will be appreciated by the person skilled in the art, when a cornea is illuminated by a stimulator point light source, four reflections (known as Purkinje images) can occur: two reflections occurring at the cornea (resulting in first and second Purkinje images) and two reflections at the lens (resulting in third and fourth Purkinje images). As the fourth Purkinje image is an inverted image, said image generated by a first stimulator point light source may interfere with a first or second Purkinje image of a second stimulator point light source that is diametrically opposed to the first light source. To illustrate this, FIG. 2 schematically depicts the first second and fourth Purkinje images from two diametrically opposed stimulator point light sources. In FIG. 2, reference numbers 201, 202 and 203 refer to the first, second and fourth Purkinje image of a first light source (not shown), reference numbers 205, 206 and 207 refer to the first, second and fourth Purkinje image of a second light source (not shown). As can be seen, the second and fourth Purkinje images somewhat overlap. As a consequence, it may be cumbersome to exactly locate the coordinates of the second Purkinje image, said image corresponding to the virtual image of the posterior surface of the cornea. By ensuring that the stimulator point light sources are not diametrically opposed, one can substantially reduce interference or overlap between the different Purkinje mages. A possible arrangement of the stimulator point light sources is illustrated in FIG. 3. FIG. 3 schematically depicts 21 stimulator point light sources 300 arranged on three ring shaped holders 310 that are concentrically arranged about an eye 320. The various stimulator point light sources are arranged in such manner that no light sources are diametrically opposed. One way of achieving this to ensure that each circle comprises an evenly distributed odd number of stimulator point light sources. By doing so, interference or overlap of the different Purkinje images can be mitigated or avoided.

A further factor important in establishing a model of either the anterior surface or the posterior surface is the brightness of the reflected images. In this respect, it can be noted that there is a substantial difference in brightness between the first Purkinje image (i.e. the reflection at the anterior surface of the cornea) and the second Purkinje image, the reflection at the posterior surface of the cornea. It can e.g. be observed that the brightness of the first Purkinje image can be approximately at least 100 times higher than the brightness of the second Purkinje image. Therefore, in order to accurately observe the second Purkinje image, the intensity of the stimulator point light sources should be made sufficiently high.

In order to facilitate determining the coordinates of the reflected images of the stimulator point light sources, it is preferred that the contrast between the reflected image and the background is as large as possible. One way to achieve this is to ensure that the orientation and beam width of the rays from each stimulator point light source is such that the iris of the eye is not or barely illuminated. As such, reflections from the iris can be mitigated or avoided thereby improving the contrast of the reflections on the image. As an alternative, the pupil could be dilated prior to the capturing of an image or images, thereby increasing the pupil, which provides a dark background and therefore a good contrast for determining locations of the second Purkinje images.

As already mentioned above, the apparatus according to the invention may equally be applied to derive a model for the anterior surface. In order to obtain such model representing the anterior surface, there is no need to observe the second Purkinje image as it represents a reflection of the posterior surface. In such a situation, it may be advantageous to apply a reduced intensity of the stimulator point light sources. This is illustrated in the following FIG. 4.

In case the corneal surface of an eye is illuminated by a stimulator point light source, the reflected image as received by the camera system may look like a spot of a certain diameter (e.g. due to optical aberrations and non-zero size of point source). In order to determine a model of the anterior surface as accurately as possible, the coordinates of the intersection of the ray of light originating from the stimulator point light source with the anterior surface should be determined as accurately as possible. This intersection point can be derived using the location of the captured first Purkinje image spot on the camera. When the pixels in this spot are substantially overfilled (many pixels will have the maximum grey level), the spot appears on the image as a spot with a substantially uniform brightness, taking the coordinates of the centroid of the spot as the required coordinates would actually be the only available option. When the image is made with a reduced intensity however, (as would be acceptable since the reflections on the posterior surface need not be determined) the spot may appear as having a varying intensity over its area. In such a situation, the required coordinates can be determined as the position having the highest intensity, thereby providing a more accurate position of the point of intersection of the ray of light originating of the stimulator point light source with the anterior surface.

Figure 4:
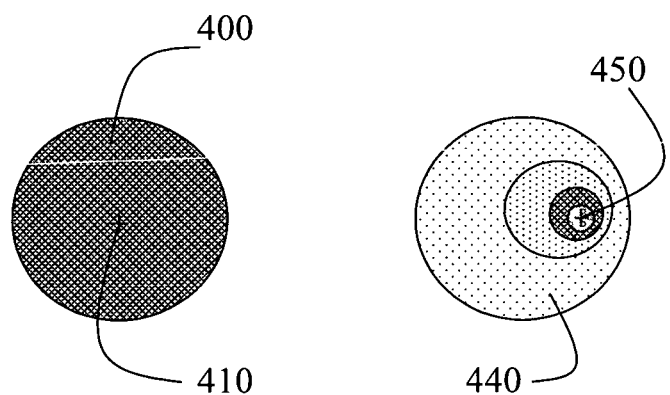
FIG. 4 schematically depicts a reflected image of a stimulator point light source at a high intensity value and at a low intensity value.

FIG. 4 therefore schematically depicts on the left a spot 400 of certain size having a uniform intensity (or brightness) together with the estimated intersection point 410 (i.e. the centre point of the spot). On the right, an image of a similar spot 440, obtained by illuminating the cornea with a reduced intensity, said spot having a varying intensity over its area (indicated by the different patterns). Indicated by 450 is the selected intersection point as the point having the highest intensity. As can be noticed, by capturing an image of reduced intensity, a more accurate determination of the location of the Purkinje image on the camera can be made leading to an accurate calculation of the intersection. It will be appreciated by the skilled person that a more accurate determination of the coordinates of the intersection of the ray of light originating of the stimulator point light source with the anterior surface can result in a more accurate model of the anterior surface. As the determination of the model of the posterior surface relies on the model of the anterior surface, the accuracy of the anterior surface model will affect the accuracy of the posterior surface model and consequently also the accuracy of the corneal thickness.

Figure 5:
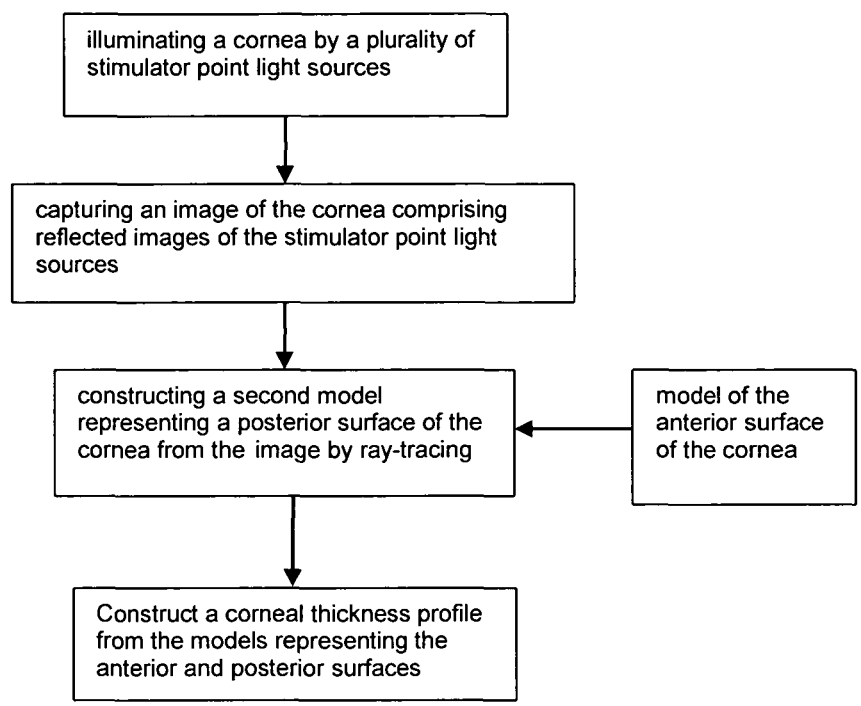
FIG. 5 schematically depicts a flow chart of an embodiment of the method according to the present invention.

As already mentioned, the present invention provides in a method for determining a corneal thickness. FIG. 5 schematically describes a flow chart of an embodiment of the method according to the present invention. In a first step, a cornea is illuminated by a plurality of stimulator point light sources. In a next step, an image of the cornea comprising reflected images of the stimulator point light sources is captured, e.g. by a CCD camera. In the method according to the invention, the captured image is used to determine a model of the posterior corneal surface using a model of the anterior surface combined with ray-tracing techniques. The anterior surface model can be obtained from either a separate measurement using a corneal topographer or can be obtained using the apparatus according to the invention. The latter case may provide additional advantages as it enables the model representing the anterior surface to be more accurate compared to a model obtained from a conventional Placido based topographer. As will be appreciated by the skilled person, a more accurate model of the anterior surface can enable the posterior corneal surface to be determined with a higher accuracy.

As an example on how a model can be obtained representing the anterior surface of the cornea, reference can be made to the J. Opt. Soc. Am. A/Vol. 21, No. 7, /July 2004, "Corneal surface reconstruction algorithm that uses Zernike polynomial representation".

In general, the reflections of a stimulator source on the anterior corneal surface are detected from an image taken by the camera system. From the geometry of the apparatus, the known geometry of the stimulator source and the observed reflections, the corneal apex point can be determined. This point is used as a reference point for reconstructing the corneal surfaces. Once the apex point is determined, any suitable mathematical model can be referenced to this reference point and used to model the anterior surface. Several options exist for modelling either the anterior or the posterior surface.

As an example, a tonic aspheric model can be applied. In cylindrical coordinates $\rho$, $\theta$, z, the model can be described as:

$$z^2 - 2rz + k\rho^2 = 0$$

$$r = r_0 - \delta r \cos^2(\theta - \alpha) \quad (1)$$

Where k is the asphericity, r is the meridian radius of curvature, $r_0$ is the maximum radius of curvature, $\delta r$ is the toricity and $\alpha$ is the axis of astigmatism.

A polynomial series expansion (i.e. Zernike, Taylor) is another example on how to model the corneal surfaces.

The parameters of the mathematical model can be determined from the known geometry of the apparatus and the reflected images of the stimulator source. When stimulator point light sources are applied, ray tracing can be applied to determine the parameters of the mathematical model. This can be done using the following conditions:

the ray of light originating from the stimulator point light source and the reflected ray towards the camera system need to fulfil the law of specular reflection; the angle of the anterior surface normal with the incident ray (ray originating from the stimulator source) should be equal to the angle between the anterior surface normal and the reflected ray.

the intersection point of the incident ray and the reflected ray is a point on the anterior surface.

The principle as described can be applied for each of the plurality stimulator point light sources thereby obtaining the coordinates of a plurality of points on the anterior surface of the cornea. A least squares fitting can then be done using the mathematical model and the reflection restrictions to determine the exact points of reflection on the anterior corneal surface. As a result, a model of the anterior corneal surface in terms of asphericity (k-value) and toricity (maximum radius, minimum radius and axis) can be obtained.

It can be noted that by analysing the stimulator point light source reflections by algorithms based on ray tracing as described above, a more accurate model is obtained compared to known algorithms based on paraxial analysis. In principle, paraxial analysis is an approximation using spherical model of the cornea. Ray tracing methods for an asphericity of k=0.47 for the anterior surface describe a surface that will give exactly the same results as the paraxial model. Other asphericity values will lead to different results. The average corneal asphericity is 0.9 and therefore the paraxial model is not enough.

Once a model for the anterior surface is obtained, a model for the posterior surface can be determined using ray-tracing techniques. An example of ray-tracing techniques as applied in the present invention is illustrated in FIG. 6.

Figure 6:
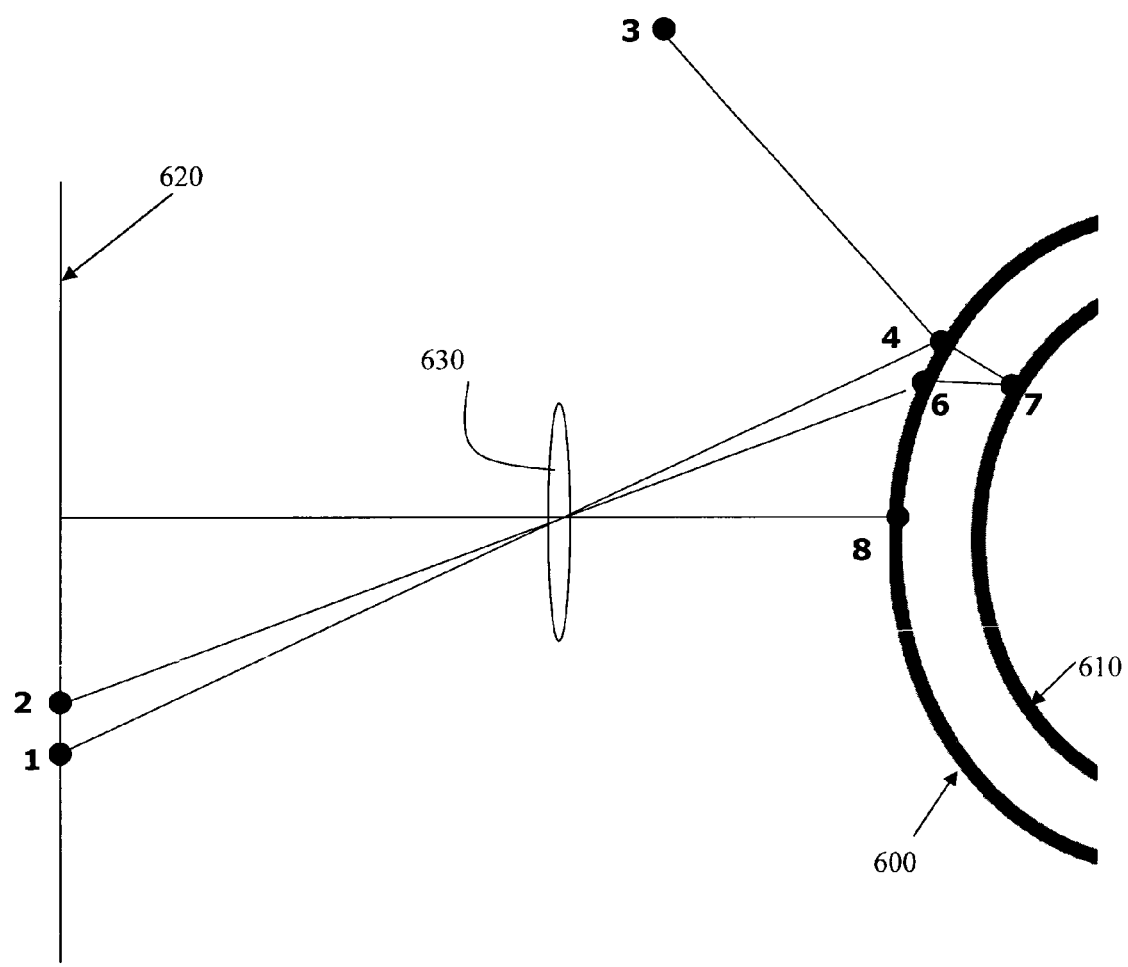
FIG. 6 schematically illustrates an embodiment of the use of ray-tracing to obtain a model of the posterior surface of the cornea as applied in the present invention.

FIG. 6 schematically depicts the anterior 600 and posterior 610 surfaces of a cornea, a stimulator point light source 3, a ray of light 3-4 originating from a stimulator point light source and the reflected rays of said ray of light on both the anterior and posterior surface, said reflected rays being captured by a camera system 620. FIG. 6 further shows a lens 630 representing a nodal point of the camera system.

The coordinates of a point on the posterior surface can be determined by the following steps:

constructing a first ray 1-4 originating from the first Purkinje image 1 of the stimulator point light source 3 towards the cornea, determining a first intersection point 4 as the intersection of the first ray with the model representing the anterior surface.

construct a second ray 2-6 originating from the second Purkinje image 2 of the stimulator point 3 towards the cornea, determining a second intersection point 6 as the intersection of the second ray with the model representing the anterior cornea, constructing a first refracted ray 4-7 from the first ray into the cornea originating from the first intersection point, using Snell's Law and the model representing the anterior cornea, constructing a second refracted ray 6-7 from the second ray into the cornea originating from the second intersection point, using Snell's Law and the model representing the anterior cornea, determine a point on the posterior surface as the intersection of the first and second refracted ray.

Note that the refracted ray 4-7 may equally be determined from the refraction of the ray originating from the stimulator point light source 3-4. The coordinates of a point on the posterior surface can then be determined by the following steps;

constructing a first ray 3-4 originating from the stimulator point light source 3 towards the cornea, determining a first intersection point 4 as the intersection of the first ray with the model representing the anterior surface.

construct a second ray 2-6 originating from the second Purkinje image 2 of the stimulator point 3 towards the cornea, determining a second intersection point 6 as the intersection of the second ray with the model representing the anterior cornea, constructing a first refracted ray 4-7 from the first ray into the cornea originating from the first intersection point, using Snell's Law, constructing a second refracted ray 6-7 from the second ray into the cornea originating from the second intersection point, using Snell's Law, determine a point on the posterior surface as the intersection of the first and second refracted ray.

Figure 7:
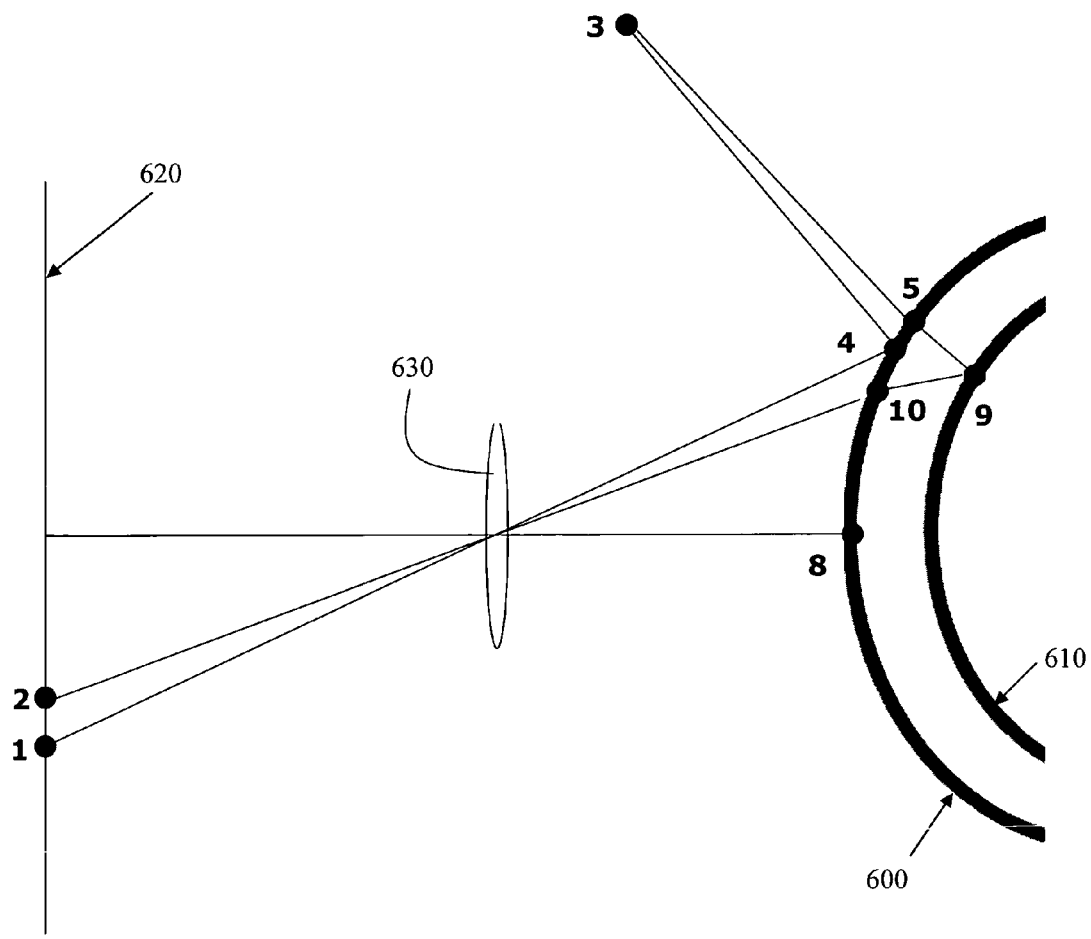
FIG. 7 schematically illustrates a preferred embodiment of the use of ray-tracing to obtain a model of the posterior surface of the cornea as applied in the present invention.

FIG. 6 illustrates ray tracing corresponding to a source producing a collimated beam. If the light source does not produce a collimated beam, the chief ray for the $2^{nd}$ Purkinje image may take a different path as illustrated in FIG. 7 (Path 3-5-9-10-2). The same reference number in FIG. 6 for the traced path of the first Purkinje image 1 is used. In this case, the construction of the posterior surface only requires information obtained from the second Purkinje images or reflections as long as the shape of the anterior surface is already available. Referring to FIG. 7, this means that first Purkinje image 1 is not needed for constructing the model representing the posterior surface of the cornea. The coordinates of a point on the posterior surface can e.g. be determined by the following numerical procedure. The paths 3-5, 5-9, 9-10, 10-2 can be represented by 4 vectors which will form 12 scalar equations. The model of the anterior and posterior surface forms 3 equations corresponding to points 5, 9 and 10. Two refraction events at the anterior surface will form 2 vector (6 scalar) equations obeying Snell's Law. Finally, four equations can be set-up for the reflection event at the posterior surface: 3 equations coming from the cross product reflection principle and 1 equation coming from the inner product reflection principle. All in all, these are 25 equations which are needed to determine 25 unknowns: coordinates of points 5, 9, and 10 (9 unknowns), lengths (4 unknowns) and directional cosines (12 unknowns) of the 4 ray vectors. Using standard techniques, the 25 unknowns are solved using the 25 equations.

As the brightness of the first and second Purkinje image is substantially different, this way of determining a model for the posterior surface provides an advantage as in this case, the illumination level of the stimulator point light sources can be set such that the intersection points can accurately be determined, as explained in FIG. 4.

The latter method provides a further advantage in that the camera system of the apparatus according to the present invention can set such that the second Purkinje images are in focus. In this respect, it can be noted that the first and second Purkinje images do not originate from the same plane and as such, an image comprising the first and second Purkinje images cannot have both types of images in focus.

Once the shapes of the anterior and posterior surface is available then the corneal thickness can also be determined.

Regarding the model for the anterior surface, as mentioned, this can either be obtained by known techniques such as the use of a Placido ring topographer or slit imaging systems. When data from the anterior surface is available and when the light source is a collimated beam, the determination of the shape of the posterior surface can also be derived solely from the second Purkinje images. As an example, point 4 in FIG. 6 may thus be traced directly from the source point 3 itself.

As an alternative, a reflected image of the stimulator point light sources as applied in the present method and apparatus to determine the posterior surface, may advantageously be applied to determine the anterior surface. It should be emphasised that either the same image can be applied or an image taken at a different instance. When the same image is used, it will be clear that this provides the advantage that a displacement/movement of the eye does not affect the determination of the corneal thickness. This can be considered an important advantage compared to methods requiring multiple images taken at different instances (e.g. when different illuminator sources are used). The latter case may however also provide an advantage in accurately assessing the coordinates of the light source image on the captured image, as is illustrated in FIG. 4.

It should also be noted that 'light' within the meaning of the present invention is not limited to visible light, in a preferred embodiment, the stimulator point light sources provide IR light.

The invention claimed is:

1. A method of determining a corneal thickness comprising the steps of:
   illuminating a cornea by a plurality of stimulator point light sources arranged along a plurality of concentric diameters, with no two stimulator point light sources being diametrically opposed,
   capturing an image of the cornea comprising reflected images of the stimulator point light sources,
   obtaining a model representing an anterior surface of the cornea,
   constructing a second model representing a posterior surface of the cornea from the image by ray-tracing the reflected images of the stimulator point light sources towards the model representing the anterior surface of the cornea, and
   determining the corneal thickness from the model representing the anterior surface and the second model representing the posterior surface.

2. The method according to claim 1 wherein the reflected images of the stimulator point light sources comprise first and second Purkinje images.

3. The method according to claim 2 wherein the step of constructing the second model representing the posterior surface comprises:
   for one or more of the stimulator point light sources:
   constructing a first ray originating from the stimulator point light source towards the cornea,
   determining a first intersection point as the intersection of the first ray with the model representing the anterior surface of the cornea,
   construct a second ray originating from the second Purkinje image of the stimulator point light source towards the cornea,
   determining a second intersection point as the intersection of the second ray with the model representing the anterior surface of the cornea,
   constructing a first refracted ray from the first ray into the cornea originating from the first intersection point, using Snell's Law,
   constructing a second refracted ray from the second ray into the cornea originating from the second intersection point, using Snell's Law, and
   determining a point on the posterior surface as the intersection of the first and second refracted ray.

4. The method according to claim 1 wherein the reflected images of the stimulator point light sources comprise second Purkinje images.

5. The method according to claim 4 wherein the step of constructing the second model representing the posterior surface comprises:
   for one or more of the stimulator point light sources:
   constructing a first ray originating from the stimulator point light source towards the cornea,
   determining a first intersection point as the intersection of the first ray with the model representing the anterior surface of the cornea,
   constructing a second ray originating from the second Purkinje image of the stimulator point towards the cornea,
   determining a second intersection point as the intersection of the second ray with the model representing anterior surface of the cornea,
   constructing a first refracted ray from the first ray into the cornea originating from the first intersection point, using Snell's Law,
   constructing a second refracted ray from the second ray into the cornea originating from the second intersection point, using Snell's Law, and
   determining a point on the posterior surface as the intersection of the first and second refracted ray.

6. The method according to claim 1 wherein the model of the anterior surface of the cornea is determined using a corneal topographer.

7. The method according to claim 1 wherein the model representing the anterior surface of the cornea is obtained by:
   capturing a corneal image obtained by illuminating the cornea with a stimulator source,
   using ray-tracing to determine a point of reflection of the stimulator source on the anterior surface, and
   performing a fitting algorithm of the point of reflection to a mathematical model to obtain the model representing the anterior surface of the cornea.

8. The method according to claim 7 wherein the image of the cornea is used as the corneal image.

9. The method according to claim 8 wherein the corneal image is obtained by illuminating the cornea by the plurality of stimulator point light sources with a lower illumination level as the image of the cornea.

10. The method according to claim 1 wherein a toric aspheric model is used as the model representing the anterior surface.

11. The method according to claim 1 wherein the model representing the anterior surface comprises a plurality of Zernike polynomials.

12. The method according to claim 1, wherein each of the plurality of stimulator point light sources arranged along a plurality of concentric diameters is circumferentially offset from a nearest point light source on an adjacent diameter.

13. The method according to claim 1, wherein each of the plurality of stimulator point light sources arranged along a plurality of concentric diameters is circumferentially offset substantially equidistant to either side from a nearest point light source arranged on its own diameter.

14. The method according to claim 1, wherein the plurality of stimulator point light sources comprises an odd number of stimulator point light sources arranged along each concentric diameter.

15. The method according to claim 1, wherein the plurality of stimulator point light sources are distributed substantially equally among the plurality of concentric diameters.

16. An apparatus for corneal shape analysis comprising a plurality of stimulator point light sources arranged along a plurality of concentric diameters, with no two stimulator point light sources being diametrically opposed, for, in use, illuminating a cornea of an eye, a camera system for capturing reflected images of the stimulator point light sources, a computational unit for, in use, performing the following steps obtaining a model of an anterior surface of the cornea, constructing a second model representing the posterior surface of the cornea by ray-tracing the reflected images of the stimulator point light sources towards the model representing the anterior surface of the cornea and determining a corneal thickness from the model representing the anterior surface and the second model representing the posterior surface.

17. The apparatus according to claim 16 wherein the camera system is arranged to capture a first image comprising reflected images of the stimulator point light sources and to capture a second image comprising reflected images of the stimulator point light sources, the computational unit further being arranged to, in use, obtain the model of an anterior surface of the cornea using the first image and construct the second model representing the posterior surface using the second image.

18. The apparatus according to claim 17, wherein the apparatus further comprises a control unit for setting an illumination level of the stimulator point light sources thereby enabling the first and second image to be captured with a different illumination level.

19. The apparatus according to claim 18, wherein the control unit is further arranged to selectively enable the stimulator point light sources.

20. The apparatus according to claim 18, the apparatus further being arranged to compare a position of iris features on the first and second image in order to determine the presence or absence of substantial eye movements.

21. The apparatus according to claim 16 wherein the stimulator point light sources comprise a LED or a laser diode.

22. The apparatus according to claim 16 wherein the stimulator point light sources originate from a collimated light source.

23. The apparatus according to claim 16 wherein the plurality of stimulator point light sources are distributed along one or more concentric circles.

24. The apparatus according to claim 23 wherein each circle comprises an evenly distributed odd number of stimulator point light sources.

25. The method according to claim 16, wherein each of the plurality of stimulator point light sources arranged along a plurality of concentric diameters is circumferentially offset from a nearest point light source on an adjacent diameter.

26. The method according to claim 16, wherein each of the plurality of stimulator point light sources arranged along a plurality of concentric diameters is circumferentially offset substantially equidistant to either side from a nearest point light source arranged on its own diameter.

27. The method according to claim 16, wherein the plurality of stimulator point light sources comprises an odd number of stimulator point light sources arranged along each concentric diameter.

28. The method according to claim 16, wherein the plurality of stimulator point light sources are distributed substantially equally among the plurality of concentric diameters.

* * * * *